US009102926B2

(12) United States Patent
Isop et al.

(10) Patent No.: US 9,102,926 B2
(45) Date of Patent: Aug. 11, 2015

(54) COMPOSITIONS AND METHODS FOR DEGRADING LIGNOCELLULOSIC BIOMASS

(75) Inventors: Cathy Isop, Lunel (FR); Pascale Joesph, Montpellier (FR); Jean-Paul Leonetti, Castelnau-le-Lez (FR); Jacques Biton, Lacroix-Saint-Ouen (FR)

(73) Assignees: DEINOVE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 184 days.

(21) Appl. No.: 13/201,926

(22) PCT Filed: Feb. 16, 2010

(86) PCT No.: PCT/EP2010/051885
§ 371 (c)(1),
(2), (4) Date: Aug. 17, 2011

(87) PCT Pub. No.: WO2010/094665
PCT Pub. Date: Aug. 26, 2010

(65) Prior Publication Data
US 2011/0306085 A1 Dec. 15, 2011

Related U.S. Application Data

(60) Provisional application No. 61/153,478, filed on Feb. 18, 2009.

(30) Foreign Application Priority Data

Feb. 17, 2009 (EP) .................................... 09305154

(51) Int. Cl.
| | | |
|---|---|---|
| C12N 1/20 | (2006.01) | |
| C12P 1/04 | (2006.01) | |
| C12N 15/01 | (2006.01) | |
| C12P 7/10 | (2006.01) | |

(52) U.S. Cl.
CPC ...... *C12N 1/20* (2013.01); *C12N 15/01* (2013.01); *C12P 1/04* (2013.01); *C12P 7/10* (2013.01); *Y02E 50/16* (2013.01); *Y02E 50/17* (2013.01)

(58) Field of Classification Search
CPC ..... C12P 1/04; C12P 2201/00; C12P 2203/00
USPC ..................... 435/41, 72, 71.1, 170
See application file for complete search history.

(56) References Cited

U.S. PATENT DOCUMENTS

| 5,658,765 A * | 8/1997 | Noguchi et al. ................. 435/99 |
| 6,102,690 A | 8/2000 | Ingram et al. |
| 6,346,407 B1 | 2/2002 | DeBuyl et al. |
| 6,406,690 B1 * | 6/2002 | Peleg et al. ................. 424/93.46 |
| 2011/0104766 A1 | 5/2011 | Leonetti et al. |
| 2011/0294979 A1 | 12/2011 | Leonetti et al. |
| 2012/0052540 A1 | 3/2012 | Biton et al. |
| 2012/0058533 A1 | 3/2012 | Biton et al. |

FOREIGN PATENT DOCUMENTS

| EP | 2218773 | 8/2010 |
| KR | 100836093 | 6/2008 |
| WO | WO 95/27064 | 10/1995 |
| WO | WO 97/10352 | 3/1997 |
| WO | WO 01/23526 | 4/2001 |
| WO | WO 02/059351 | 8/2002 |
| WO | WO 2006/131734 | 12/2006 |
| WO | WO 2007/128338 | 11/2007 |
| WO | WO 2009/063079 | 5/2009 |
| WO | WO 2010/081899 | 7/2010 |
| WO | WO 2010/130806 | 11/2010 |
| WO | WO 2010/130812 | 11/2010 |
| WO | WO2011/107506 | 9/2011 |

OTHER PUBLICATIONS

Zhang, Y.-M. et al. "Induction of a Futile Embden-Meyerhof-Parnas Pathway in *Deinococcus radiodurans* by Mn: Possible Role of the Pentose Phosphate Pathway in Cell Survival" *Applied and Environmental Microbiology*, Jan. 2000, pp. 105-112, vol. 66, No. 1.
Holland, A. et al. "Development of a defined medium supporting rapid growth for *Deinococcus radiodurans* and analysis of metabolic capacities" *Applied Microbiology and Biotechnology*, Mar. 31, 2006, pp. 1074-1082, vol. 72, No. 5.
Anonymous. "Conference de presse: Présentation des projets de DEINOVE dans le domaine des biocarburants et des activités de DEINOLAB, laboratoire coopératif créé par DEINOVE, le CNRS et l'Université de Montpellier" Oct. 15, 2008, pp. 1-10, XP-002591932.
Written Opinion in International Application No. PCT/EP2010/056592, Jul. 29, 2010, pp. 1-7.
Makarova, K. et al. "Genome of the Extremely Radiation-Resistant Bacterium *Deinococcus radiodurans* Viewed from the Perspective of Comparative Genomics" *Microbiology and Molecular Biology Reviews*, Mar. 2001, pp. 44-79, vol. 65, No. 1.
Omelchenko, M. et al. "Comparative genomics of *Thermus thermophilus* and *Deinococcus radiodurans*: divergent routes of adaptation to thermophily and radiation resistance" *BMC Evolutionary Biology*, 2005, pp. 1-22, vol. 5, No. 57.

(Continued)

*Primary Examiner* — Ruth Davis
(74) *Attorney, Agent, or Firm* — Saliwanchik, Lloyd & Eisenschenk

(57) ABSTRACT

The present invention relates to compositions and methods of producing bioenergy products and metabolites of industrial interest from lignocellulosic biomass. More specifically, the invention describes the identification, characterization and isolation of novel bacteria having the remarkable ability to transform lignocellulosic biomass into fermentable sugars and, even more remarkably, into bioenergy products and metabolites. The invention also discloses a method to isolate such bacteria, compositions comprising such bacteria, and their uses for the modification of lignocellulosic biomass, with a view to producing bioenergy.

11 Claims, 2 Drawing Sheets

(56) References Cited

OTHER PUBLICATIONS

Rainey, F. et al. "Extensive Diversity of Ionizing-Radiation-Resistant Bacteria Recovered from Sonoran Desert Soil and Description of Nine New Species of the Genus *Deinococcus* Obtained from a Single Soil Sample" *Applied and Environmental Microbiology*, Sep. 2005, pp. 5225-5235, vol. 71, No. 9.

Weisburg, W.G. et al. "The *Deinococcus-Thermus* Phylum and the Effect of rRNA Composition on Phylogenetic Tree Construction" *Systematic and Applied Microbiology*, 1989, pp. 128-134, vol. 11.

Database EMBL, Accession No. M21413, "*D. radiodurans* 16s ribosomal RNA gene" XP002633260, Nov. 23, 1989, p. 1.

Suihko, M.L. et al. "Characterization of aerobic bacterial and fungal microbiota on surfaces of historic Scottish monuments" *Systematic and Applied Microbiology*, 2007, pp. 494-508, vol. 30.

Database EMBL, Accession No. EF093134, "*Deinococcus* sp. VTT E-052909 16S ribosomal RNA gene, complete sequence" XP002633261, Aug. 7, 2007, pp. 1-2.

Database EMBL, Accession No. AM283039, "*Deinococcus* sp. Han23 partial 16S rRNA gene, strain Han23" XP002633262, Jun. 26, 2006, p. 1.

Rainey, F. et al. "Phylogenetic Diversity of the Deinococci as Determined by 16S Ribosmal DNA Sequence Comparison" *International Journal of Systemic Bacteriology*, Apr. 1997, pp. 510-514, vol. 47, No. 2.

Written Opinion in International Application No. PCT/EP2011/053089, Mar. 2, 2010, pp. 1-7.

Brim, H. et al. "Engineering *Deinococcus radiodurans* for metal remediation in radioactive mixed waste environments" *Nature Biotechnology*, Jan. 2000, pp. 85-90, vol. 18, XP-002491111.

Henstra, A. M. et al. "Microbiology of synthesis gas fermentation for biofuel production" *Current Opinion in Biotechnology*, 2007, pp. 200-206, vol. 18, XP-22110181.

John, R. P. et al. "Fermentative production of lactic acid from biomass: an overview on process developments and future perspectives" *Appl. Microbiol. Biotechnol.*, 2007, pp. 524-534, vol. 74, XP-002464997.

Klapatch, T. R. et al. "Organism Development and Characterization for Ethanol Production Using Thermophilic Bacteria" *Applied Biochemistry and Biotechnology*, 1994, pp. 209-223, vol. 45/46, XP-009104255.

Lynd, L. R. "Production of Ethanol from Lignocellulosic Materials Using Thermophilic Bacteria: Critical Evaluation of Potential and Review" *Advances in Biochemical Engineering*, 1989, pp. 1-52, vol. 38, XP-9104256.

Makarova, K. S. et al. "*Deinococcus geothermalis*: The Pool of Extreme Radiation Resistance Genes Shrinks" *PLOS ONE*, Sep. 2007, pp. 1-21, vol. 9, XP-002491112.

Meima, R. et al. "Promoter Cloning in the Radioresistant Bacterium *Deinococcus radiodurans*" *Journal of Bacteriology*, May 2001, pp. 3169-3174, vol. 183, No. 10, XP-002491110.

Smith, M. D. et al. "Gene expression in *Deinococcus radiodurans*" *Gene*, 1991, pp. 45-52, vol. 98, XP-002938523.

Zahradka, K. et al. "Reassembly of shattered chromosomes in *Deinococcus radiodurans*" *Nature*, Oct. 5, 2006, pp. 569-573, vol. 443, XP-002491114.

Office Action dated Nov. 8, 2012 in U.S. Appl. No. 12/740,404.

Fontaine, L. et al. "Molecular Characterization and Transcriptional Analysis of *adhE2*, The Gene Encoding the NADH-Dependent Aldehyde/Alcohol Dehydrogenase Responsible for Butanol Production in Alcohologenic Cultures of *Clostridium acetobutylicum* ATCC 824" *Journal of Bacteriology*, Feb. 2002, pp. 821-830, vol. 184, No. 3.

Skory, C. D. "Isolation and Expression of Lactate Dehydrogenase Genese from *Rhizopus oryzae*" *Applied and Environmental Microbiology*, Jun. 2000, pp. 2343-2348, vol. 66, No. 6.

Berdy, J. "Bioactive Microbial Metabolites—A personal view" *Journal of Antibiotics*, Jan. 1, 2005, pp. 1-26, vol. 58, No. 1.

Singh, S. et al. "Biodiversity, chemical diversity and drug discovery" *Progress in Drug Research*, 2008, pp. 142-174, vol. 65.

Yang, B. et al. "Effects of microwave irradiation on isolation of soil actinomycetes" *Yingyong Shengtai Xuebao*, May 2008, pp. 1091-1098, vol. 19, No. 5.

Sinha, R. et al. "UV-protectants in cyanobacteria" *Plant Science*, Dec. 23, 2007, pp. 278-289, vol. 174, No. 3.

Chung, B. et al. "Effects of low-dose gamma-irradiation on production of shikonin derivatives in callus cultures of *Lithospermum erythrorhizon* S." *Radiation Physics and Chemistry*, Sep. 1, 2006, pp. 1018-1023, vol. 75, No. 9.

Ghosal, D. et al. "How radiation kills cells: Survival of *Deinococcus radiodurans* and *Shewanella oneidensis* under oxidative stress" *FEMS Microbiology Reviews*, Apr. 2005, pp. 361-375, vol. 29.

Dib, J. et al. "Occurrence of Resistance to Antibiotics, UV-B, and Arsenic in Bacteria Isolated from Extreme Environments in High-Altitude (Above 4400 m) Andean Wetlands" *Current Microbiology*, May 2008, pp. 510-517, vol. 56, No. 5.

Keller, M. et al. "Tapping Into Microbial Diversity" *Nature Reviews*, Feb. 2004, pp. 141-150, vol. 2, No. 2.

Reichenbach, H. "Myxobacteria, producers of novel bioactive substances" *Journal of Industrial Microbiology & Biotechnology*, Jan. 1, 2001, pp. 149-156, vol. 27. No. 3.

Bibb, M. "Regulation of secondary metabolism in streptomycetes" *Current Opinion in Microbiology*, 2005, pp. 208-215, vol. 8, No. 2.

Written Opinion in International Application No. PCT/EP2010/050513, Apr. 24, 2010, pp. 1-10.

Kolari, M. et al. "Colored moderately thermophilic bacteria in paper-machine biofilms" *Journal of Industrial Microbiology and Biotechnology*, Apr. 2003, pp. 225-238, vol. 30, No. 4.

Written Opinion in International Application No. PCT/EP2010/056600, May 14, 2009, pp. 1-8.

Ferreira, A. et al. "*Deinococcus geothermalis* sp. nov. and *Deinococcus murrayi* sp. nov., Two Extremely Radiation-Resistant and Slightly Thermophilic Species from Hot Springs" *International Journal of Systematic Bacteriology*, Oct. 1997, pp. 939-947, vol. 47, No. 4.

Written Opinion in International Application No. PCT/EP2008/065613, Jan. 28, 2009, pp. 1-8.

Harish, V. et al. "Xylanase Production by Ultra Violet Induced Variants of *Streptomyces fradiae* SCF-5" *Journal of Food Science and Technology*, Jan. 1, 1978, pp. 243-246, vol. 15, No. 6.

Alea, F, et al. "Selection of hypercellulolytic derepressed mutants of *Cellulomonas* sp." *Applied Microbiology and Biotechnology*, 1991, pp. 643-645, vol. 35, No. 5.

Temp, U. et al. "A Small-Scale Method for Screening of Lignin-Degrading Microorganisms" *Applied Environmental Microbiology*, Apr. 1998, pp. 1548-1549, vol. 64, No. 4.

Zenoff, V. F. et al. "Diverse UV-B Resistance of Culturable Bacterial Community from High-Altitude Wetland Water" *Current Microbiology*, May 1, 2006, pp. 359-362, vol. 52, No. 5.

Weon, H.-Y. et al. "*Deinococcus cellulosilyticus* sp. nov., isolated from air" *International Journal of Systematic and Evolutionary Microbiology*, Aug. 2007, pp. 1685-1688, vol. 57, Part 8.

Pavlikova, E. et al. "Improvement of the Basidiomycete *Coprinus* sp." *Folia Microbiologica*, Jan. 1, 1982, pp. 126-130, vol. 27, No. 2.

Written Opinion in International Application No. PCT/EP2010/051885, Aug. 23, 2010, pp. 1-10.

Enoki, A. "Lignin Decomposition by Microorganisms", *Wood Research Documents*, Dec. 1981, pp. 1-15, No. 16.

\* cited by examiner

COMPOSITIONS AND METHODS FOR DEGRADING LIGNOCELLULOSIC BIOMASS

CROSS-REFERENCE TO RELATED APPLICATIONS

This application is the U.S. national stage application of International Patent Application No. PCT/EP2010/051885, filed Feb. 16, 2010, which claims the benefit of U.S. Provisional Patent Application No. 61/153,478, filed Feb. 18, 2009, the disclosures of which are hereby incorporated by reference in their entireties, including all figures, tables and amino acid or nucleic acid sequences.

The present invention relates to composition and methods of producing bioenergy products and metabolites of industrial interest from lignocellulosic biomass. More specifically, the invention describes the identification, characterization and isolation of novel bacteria having the remarkable ability to transform lignocellulosic biomass into fermentable sugars and, even more remarkably, into bioenergy products and metabolites. The invention also discloses a method to isolate such bacteria, compositions comprising such bacteria, and their uses for the modification of lignocellulosic biomass, with a view to producing bioenergy.

BACKGROUND

The conversion of lignocellulosic biomass has been the subject of intense research efforts since the 1970s (Blumer-Schuette et al., 2008, Extremely thermophilic microorganisms for biomass conversion: status and prospects, Curr Opinion Biotechnol 19, pp. 210-217; Perez et al., 2002, Int Microbiol 5, pp 53-63).

In this regard, it is known to use microorganisms to conduct modification of transformed biomass, essentially pre-treated agricultural feedstocks, to produce bioenergy products such as ethanol. As reported in Mosier et al. (Bioresource Technology 96 (2005) 673-686), however, the pre-treatment of lignocellulosic biomass is required to alter the structure of cellulosic biomass to make cellulose more accessible to the enzymes that convert the carbohydrate polymers into fermentable sugars.

It is believed, however, that future bio fuels or bioenergy products should originate from raw lignocellulosic biomass, instead of from pre-treated agricultural feedstocks. The use of such raw biomass would require an effective method of degrading (e.g., hydrolysing) lignocellulosic biomass into fermentable sugars, which can then be transformed through fermentation into bioenergy products (e.g., alcohols and other metabolites of industrial value). The production of fermentable sugars (e.g., monomeric sugars) from raw lignocellulosic biomass, is therefore a major challenge, and various approaches have been proposed in this regard, such as thermochemical methods, acid hydrolysis and enzymatic hydrolysis.

However, due to the wide range of lignocellulosic biomass being considered, with each having a specific composition of cellulose, hemicellulose and lignin, the development of enzymes or enzymatic compositions for hydrolysing such a raw biomass does not appear cost-effective. In addition, lignin by-products remaining from such treatments of lignocellulosic biomass generally remain unmodified and lost.

WO2009/063079 describes the use of bacteria of the genus *Deinococcus* for the production of bioenergy products and metabolites through fermentation of biomass.

Taryn et al (ABB 45 (1994) 209) reports the ability of bacteria of the genus *Clostridium* for degrading fermentable sugars.

WO97/10352 relates to *Pseudomonas* bacterial strains that degrade cellulose. Similarly, Weon et al (Int. J. Systematic and Evolutionary Microbiology (2007), 57, pp 1685-1688) reports UV-resistant *Deinococcus* strains which hydrolyse cellulose.

W. Zimmermann (Journal of Biotechnology, 13 (1990) 119-130) provides a review of bacterial degradation of lignin.

Bacteria having the ability to hydrolyse the main constituents of lignocellulosic biomass, including lignin, xylan and cellulose, under conditions suitable for an industrial process, have never been reported. In particular, bacteria which can degrade lignin under industrial conditions have never been isolated.

Accordingly, there is an unmet need for a cost-effective and scalable process for the degradation of lignocellulosic biomass into valuable products such as fermentable sugars or bioenergy products and metabolites.

SUMMARY OF THE INVENTION

The present invention relates to compositions and methods for producing valuable products from lignocellulosic biomass or derivatives thereof. More specifically, the invention relates to novel bacteria having the ability to transform lignocellulosic biomass or derivatives thereof into valuable products, including fermentable sugars and bioenergy products. The invention also relates to methods of producing valuable products and metabolites using such bacteria.

The invention derives inter alia from the identification of microorganisms having the unexpected and remarkable properties of transforming lignocellulosic biomass or derivatives thereof, with a view to obtaining compounds which can be used to produce bioenergy, ethanol in particular, on an industrial scale and both economically and reliably.

In this regard, the invention results from the design of an improved method of selecting or identifying bacterium from any sample. More particularly, the present invention discloses a method of selecting or identifying or isolating a bacterium, the method comprising the following steps:

a) providing a sample comprising bacteria;
b) subjecting the sample to a cell-destructing DNA damaging treatment; and
c) selecting or isolating, from said treated sample, a bacterium which has the ability to live or grow in the presence of lignin, cellulose or xylan as a carbon source, e.g., to use lignin, cellulose or xylan as carbon source.

A further object of this invention is a bacterium obtainable by such a method, or an extract of said bacterium.

Following the above method, the inventors have indeed isolated and identified from raw materials new microorganisms having the unexpected capacity of hydrolysing the three main components of the lignocellulosic biomass, i.e., cellulose, xylan and lignin.

This new finding that a microorganism is able to transform lignin-containing raw material for the production of bio-energy products represents a technological breakthrough by allowing a single-step production process of bioenergy products (e.g., ethanol) from raw biomass (lignocellulosic biomass), overcoming the previous drawbacks of using pre-treated agricultural feedstocks instead of lignocellulosic, raw biomass. Furthermore, the same bacteria of this invention may be used throughout the entire production process, i.e., to hydrolyse the lignocellulosic biomass and to produce bioenergy products by fermentation through simultaneous saccharification and fermentation process (SSF).

An object of this invention therefore resides in an isolated bacterium wherein said bacterium has the ability to grow in the presence of lignin or cellulose or xylan as a carbon source, at a temperature of 30° C. or more, and to resist an UV treatment of 4 mJ/cm2.

A particular object of this invention is an isolated bacterium wherein said bacterium has the ability to grow in the presence of lignin as sole carbon source, at a temperature of 30° C. or more, and to resist an UV treatment of 4 mJ/cm2.

Another particular object of this invention is an isolated bacterium wherein said bacterium has the ability to utilize cellulose and xylan as carbon source, at a temperature of 30° C. or more, and to resist an UV treatment of 4 mJ/cm2.

In a preferred embodiment, the bacterium of the present invention has the remarkable ability to use lignin, cellulose and xylan as carbon source. The invention indeed shows that bacteria having the ability to degrade all major constituents of lignocellulosic biomass can be identified and cultured. Such bacteria may be used to transform such biomass with unprecedented efficiency.

In a particular and preferred embodiment, the bacteria of the invention can be grown, or cultivated in both aerobic and anaerobic conditions. The invention indeed unexpectedly shows that bacteria of this invention can be operated under conditions, such as anaerobic conditions, suitable to produce high amounts of bioenergy products or metabolites from various substrates.

In a particular embodiment, the bacteria of this invention contain an exogenous nucleic acid molecule.

The bacteria of the invention belong, in a preferred embodiment, to a genus selected from *Deinococcus, Bacillus, Microbacterium, Cellulosimicrobium, Methylobacterium, Sphingobacterium, Pseudomonas, Caldimonas, Paenibacillus, Gordonia, Rhodococcus, Stenotrophomonas, Novosphingobium, Sphingomonas, Flavobacterium, Sphingobium, Sphingopyxis,* or *Porphyrobacter.*

As illustrated in the examples, bacteria of the above genus which can be identified and cultured, are able to transform biomass and to resist a cell-destructing UV treatment of 4 mJ/cm2. These bacteria represent valuable means to convert biomass, including lignocellulosic biomass, into highly valuable products.

A further object of this invention is a composition comprising a bacterium of this invention and a culture medium.

A further object of this invention is an extract of a bacterium as disclosed above.

A further object of this invention resides in the use of a bacterium of the invention, or an extract thereof, to hydrolyse lignocellulosic biomass, or to convert or transform lignocellulosic biomass into fermentable sugars.

A further object of this invention is a method of degrading or converting lignocellulosic biomass into fermentable sugars, the method comprising a step of exposing a lignocellulosic biomass to a bacterium of this invention, or an extract thereof.

A further object of this invention is a method of producing fermentable sugars from lignocellulosic biomass, the method comprising a step of exposing a lignocellulosic biomass to a bacterium of this invention or an extract thereof.

The above methods can be performed under aerobic and/or anaerobic condition, at elevated temperatures (e.g., of at least 30° C. or above), and allow the efficient transformation of all major types of constituents of lignocellulosic biomass. Furthermore, in a particular embodiment, the methods of the invention comprise a further step of either collecting the fermentable sugars, or of transforming the fermentable sugars into bioenergy products or metabolites. Such transformation (fermentation) step may be carried out using a bacterium of the invention or a distinct bacterium, or a combination of bacteria, or extracts thereof.

In a preferred embodiment, both the hydrolysis and the fermentation are performed using a bacterium of this invention, most preferably the same bacterium. Indeed, in a preferred embodiment, the invention allows the production of bioenergy products directly from lignocellulosic biomass, by allowing both hydrolysis of lignocellulosic biomass and fermentation of sugars.

A further object of this invention thus resides in the use of a bacterium of this invention to produce bioenergy products or metabolites.

Another object of this invention is a method of producing a bioenergy product or metabolite, the method comprising exposing a lignocellulosic biomass to a bacterium of this invention, or an extract thereof, and recovering the bioenergy product or metabolite obtained.

In a preferred embodiment, both the hydrolysis and the fermentation are performed using a bacterium of this invention, most preferably the same bacterium. It should be noted that, in an alternative embodiment, two or more distinct bacteria may be used, sequentially or in combination, to produce bioenergy products from lignocellulosic biomass.

In a particular aspect, the present invention relates to a method comprising the following steps:
  providing (or culturing and/or growing) a bacterium of this invention, or an extract thereof,
  modifying lignocellulosic biomass or a derivative thereof, into bioenergy products or metabolites of industrial interest (e.g., bioenergy sources such as ethanol, chemical building blocks such as succinic acid) using said bacterium or an extract thereof, and
  collecting at least one bioenergy product or metabolite resulting from said modification.

The invention also relates to a composition comprising a bacterium as defined above and a lignocellulosic biomass or a derivative thereof.

The invention also relates to bioenergy products or metabolites produced using a method as described above.

A further object of this invention is a reactor or a fermentor comprising a lignocellulosic biomass and a bacterium of this invention.

DETAILED DESCRIPTION OF THE INVENTION

Figure 1:
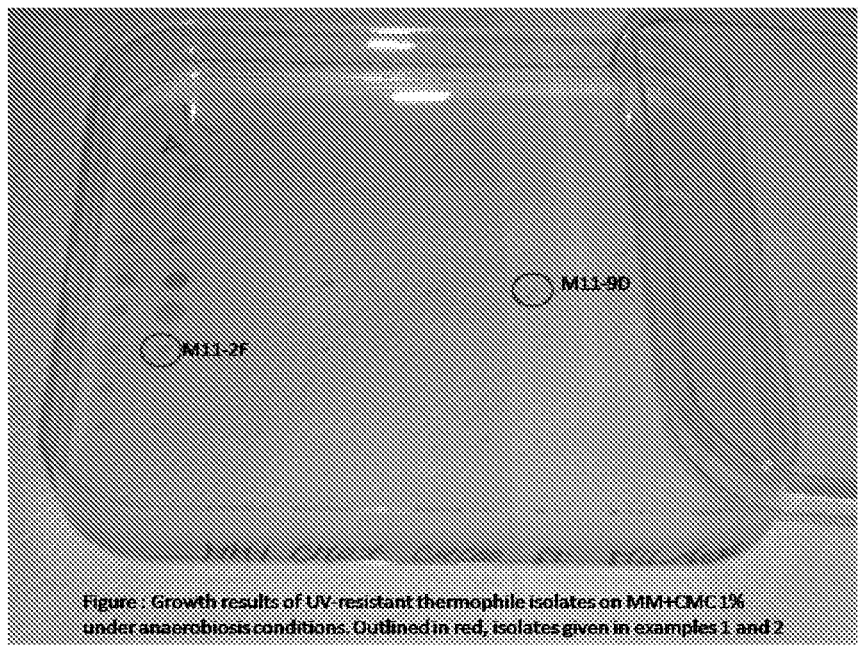
FIG. 1: growth results of UV-resistant thermophilic bacteria on MM+CMC1% under anaerobiosis conditions.

The invention describes the identification, characterization and isolation of novel bacteria having the remarkable ability to transform lignocellulosic biomass into fermentable sugars and, even more remarkably, into bioenergy products and metabolites. The invention also discloses a method to isolate such bacteria, compositions comprising such bacteria, and their uses for the modification of lignocellulosic biomass, with a view to producing bioenergy products and metabolites.

DEFINITIONS

The term lignocellulosic biomass according to the invention designates a raw biomass containing lignin, cellulose and/or xylan. The term lignocellulosic biomass thus essentially designates unprocessed material of biological origin, such as forestry products, including mature trees unsuitable for lumber or paper production, agricultural products, such as grasses, crops and animal manure, and aquatic products, such as algae and seaweed. Specific sources of biomass include, without limitation, hardwood or softwood stems, corn cobs, wheat straw, grass, leaves, seeds, paper, etc. (see for instance Sun et al., Bioresource Technology 83 (2002) 1-11). The term lignocellulosic biomass should be distinguished from transformed biomass or secondary biomass, which essentially contains hydrolysed pre-treated biomass products.

Examples of lignocellulosic biomass include wood or vegetal material derived from numerous types of plants, including miscanthus, hemp, sugarbeet, wheat, corn, poplar, willow, sorghum, sugarcane, and a variety of tree species, ranging from eucalyptus to oil palm.

As used herein, the term "biomass derivatives" designates a composition comprising molecules derived from lignocellulosic biomass, such as lignin, cellulose, hemicellulose.

In the context of the present application, the term bacteria includes wild type, or natural variant strains of a bacterium, e.g., strains obtained through accelerated evolution, by DNA-shuffling technologies, or recombinant strains obtained by insertion of eukaryotic, prokaryotic and/or synthetic nucleic acid.

An "extract of a bacterium" designates any fraction obtained from a bacterium, such as a cell supernatant, a cell debris, cell walls, DNA extract, enzymes or enzyme preparation or any preparation derived from a bacterium by chemical, physical and/or enzymatic treatment, which is essentially free of living bacteria. A bacterium extract preferably retains an enzymatic activity of the bacterium, most preferably the ability to hydrolyse lignocellulosic biomass.

Within the context of the present invention, the term "bioenergy" designates a renewable energy derived from biomass. More specifically, the term "bioenergy products" includes "biofuels" and all final products of modification of biomass or biomass derivatives that can be used as fuels, such as ethanol, propanol, butanol glycerol, butanediol and propanediol.

The term "metabolites" designates all possible intermediate molecules generated during the modification of biomass or biomass derivatives into bioenergy products, including but not limited to several chemical products of industrial interest, such as organic acids and building blocks, such as acetic acid, propionic acid, pyruvic acid, butyric acid, lactic acid and/or succinic acid.

The present invention relates to composition and methods of producing bioenergy from lignocellulosic biomass or lignocellulosic biomass derivatives. More specifically, the invention relates to the use of bacteria for the modification of lignocellulosic biomass with a view to producing bioenergy products and metabolites.

The invention now shows, for the first time, that bacteria can be isolated from environmental sources that are able to produce bioenergy products or metabolites from lignocellulosic biomass.

In this regard, an object of this invention resides in a method for isolating or identifying bacteria, comprising the following steps:
   a) providing a sample comprising bacteria;
   b) subjecting the sample to a cell destructing DNA damaging treatment; and
   c) isolating, from said treated sample, a bacterium which has the ability to live or grow in the presence of lignin, cellulose, hemicellulose or xylan as a carbon source.

The method can be implemented with various samples comprising uncharacterized bacteria, particularly with samples which are or derive from an environmental sample. Within the context of this invention, environmental samples include any sample containing (a plurality of) uncharacterized (micro)organisms, particularly uncultivated microorganisms (e.g., microorganisms that have not been purposely cultured and expanded in isolated form). The sample may be obtained or derived from natural environments or from artificial or specifically created environments.

As indicated, the sample may be any environmental sample, such as those obtained or derived from soil, water, vegetal extract, biological material, sediments, peatlands, industrial effluents or sites, mineral extracts, sand, and the like. The sample may be collected from various regions or conditions, such as but not limited to tropical regions, volcanic regions, forests, farms, industrial areas, etc. The sample usually contains various species of (uncharacterized, uncultivated) microorganisms, such as terrestrial microorganisms, marine microorganisms, freshwater microorganisms, symbiotic microorganisms, etc. Species of such environmental microorganisms include bacteria, algae, fungi, yeasts, moulds, viruses, etc. The microorganisms may include extremophile organisms, such as e.g., thermophiles. The sample typically comprises various species of such (uncultivated) microorganisms, as well as various amounts thereof. Furthermore, the sample may contain, in addition, known and/or cultivable microorganisms (e.g., prokaryotic or eukaryotic).

It should be understood that the present invention is not limited to any specific type of sample or environmental microorganism, but can be implemented using any sample comprising uncultivated microorganisms.

In a preferred embodiment, the sample is or derives from soil, water, hot springs, marine environment, mud, wood, stone, moss, vegetal extract, lichen, biological material, sediment, biofilm, industrial effluents, gas, sand, oil, sewage, or animal or human dejection.

For use in the present invention, the sample may be wet, soluble, dry, in the form of a suspension, paste, etc. Furthermore, prior to step b) of the method, the sample may be treated to improve the process, for instance to enrich for microorganisms, e.g., such as through filtration, washings, concentration, dilution, steering, drying, etc.

In a particular embodiment, the sample is in the form of a filtered suspension. More particularly, the sample may be sterile-filtered and/or placed in sterile water, prior to treatment step b).

Step b) of the process comprises subjecting the sample (i.e., microorganisms contained in the sample) to a cell destructing DNA damaging treatment.

The cell-destructing DNA damaging treatment designates a treatment that causes substantial cell death in the sample, as opposed to mere mutagenic treatments which introduce DNA modifications. In particular, the cell-destructing DNA damaging treatment is a treatment that is sufficient to cause 90% cell death, or more, in a culture of *E. coli* bacteria. Even more preferably, the cell destructing DNA damaging treatment is a treatment that is sufficient to reduce by at least 2 log the bacterial titer in a culture of *E. coli*. Surprisingly, the invention shows that such a treatment, which would normally be lethal to most cell populations, allows the efficient and rapid isolation of novel microorganisms from various types of samples, which microorganisms have unexpected properties. This result is particularly surprising since subjecting microorganisms to such cell destructing DNA damaging treatment would have been expected to prevent isolation of living microorganisms.

The DNA damaging treatment may comprise subjecting the sample to irradiation(s) and/or to one or several genotoxic agents. The treatment is conducted under conditions and/or for a period of time sufficient to induce substantial cell death in the microorganisms present in the sample.

In a particular embodiment, the DNA damaging treatment comprises subjecting the sample to one or several irradiations. A preferred treatment comprises subjecting the sample (i.e., microorganisms in the sample) to a repeated sequential irradiation treatment.

Irradiation may be selected from UV, gamma and/or X ray irradiation, either alone or in combinations, most preferably UV irradiation(s). Irradiation treatment typically comprises subjecting the microorganisms to one or several sequential irradiations (e.g., from 1 to 5), which may be of the same or different nature, preferably of the same nature.

A particularly preferred treatment comprises subjecting the sample to a cell-destructing UV irradiation. The invention indeed shows that such a treatment allows to isolate with high efficiency from environmental (e.g., soil or water) samples, under-represented bacteria species having remarkable enzymatic activities. Cell-destructing UV treatments are typically of between 0.5 and 400 mJ/cm2, more preferably of between 1 and 200 mJ/cm2, typically between 1 and 100 mJ/cm2. A preferred UV treatment is 4 mJ/cm2. Repeated irradiation treatments are typically carried out at an interval of between 1 and 8 hours, preferably 3 to 5 hours, and more preferably of about 4 hours.

In a specific embodiment, the cell-destructing DNA damaging treatment comprises subjecting the sample to at least 2, preferably at least 3 UV treatments of between 0.5 and 400 mJ/cm2 each, preferably of about 4 mJ/cm2 each, carried out at an interval of between 1 and 8 hours, preferably 3 to 5 hours, and more preferably of about 4 hours.

In an alternative method, the cell-destructing DNA damaging treatment comprises contacting the sample with a genotoxic agent, such as a solvent, mitomycin or $H_2O_2$. It should be understood that genotoxic agents may also be used in combination with irradiation.

During the treatment phase, the sample is preferably placed in a suitable culture medium such as, without limitation, PGY (Bacto-peptone 10 g/L, Yeast extract 5 g/L, glucose 1 g/L) or LB (Bacto-tryptone 10 g/L, Yeast extract 2.5 g/L, Sodium chloride 10 g/L). It should be understood that other suitable culture media are known to the skilled person (Buchanan et al, 1974, Difco, 1995) or may be prepared by the skilled person from such known media.

Treatment step b) is typically performed in a solid or semi-solid culture medium, such as in the presence of a gel (e.g., agar). A most preferred treatment medium comprises an agar culture medium, such as a soft agar culture medium. In a particular embodiment, a PGY agar medium is used to grow the bacteria. However, different solid media containing a carbon source, a nitrogen source and mineral salts can be used as well. Serial dilution techniques can also be used according to Schoenborn et al. (2004).

In step c), living or growing bacteria are identified or isolated from the treated sample. Living or growing bacteria may be identified by different means known per se in the art. In a particular embodiment, colonies which form in the culture media are identified. The living or growing bacteria can be isolated and placed in fresh medium for further culture or expansion.

In a preferred embodiment, the bacteria in step b) are cultured in a minimum medium comprising, as the sole carbon source, lignin (preferably 0.05-3% by weight), cellulose (preferably 0.5-3% by weight), and/or xylan (preferably 0.5-3% by weight). Lignin, cellulose and xylan may be obtained from commercial sources (lignin: Sigma, France; CMC and xylan: Fluka, France). Sources of minimal medium are provided in the examples. Other minimal media may be used as described previously (Rainey, F. A., et al. 2005. *Appl Environ Microbiol.* 71 (9):5225-35; Ferreira, A. C., et al, 1997. *Int J Syst Bacteriol.* 47(4):939-47; Kongpol A et al, 2008. *FEMS Microbiol Lett.* 286(2):227-235).

The methods of this invention can comprise one or several additional steps of selecting bacteria having particular properties. More particularly, in a preferred embodiment, the method further comprises one or several steps of selecting bacteria which are viable or grow under selected culture conditions, such as media, temperature, pH, salinity, nutrients, oxygenation or carbon source. For this purpose, the sample or bacteria can be placed under appropriate selection conditions during any one of steps b), or c), or during a prior or subsequent step, and the resulting property is selected for during any of these steps.

In a particular aspect of the present invention, the bacteria are cultured under particular temperature conditions in order to identify or isolate bacteria which are viable or can be grown in a temperature range from approximately 4 to 70° C. More particularly, the bacteria are maintained at the selected temperature during step b) and/or c), and/or during an additional step, in order to identify or isolate bacteria which are viable or can be grown at the desired temperature.

In another particular aspect of the present invention, the bacteria are cultured under particular saline conditions in order to identify or isolate bacteria which are viable or can be grown under concentration conditions of NaCl or equivalent salts possibly reaching around 5% weight/volume. More particularly, the bacteria are maintained at the selected salinity during step b) and/or c), and/or during an additional step, in order to identify or isolate bacteria which are viable or can be grown at the desired salinity.

In a further particular and preferred embodiment of the present invention, the bacteria are cultured under particular pH conditions in order to identify or isolate bacteria which are viable or can be grown in a pH interval between approximately 3 and 9.5, preferably between 4 and 8. More particularly, the bacteria are maintained at the selected pH during step b) and/or c); and/or during an additional step, in order to identify or isolate bacteria which are viable or can be grown at the desired pH.

In a further particular embodiment of the present invention, the bacteria are cultured under particular oxygenation conditions in order to identify or isolate bacteria which are viable or can be grown in aerobic and/or anaerobic conditions. More particularly, the bacteria are maintained under the selected oxygenation conditions during step b) and/or c); and/or during an additional step, in order to identify or isolate bacteria which are viable or can be grown at the desired conditions.

In a further particular embodiment of the present invention, the bacteria are cultured in a particular culture medium in order to identify or isolate bacteria which are viable or can be grown in the presence of a selected carbon source. More particularly, the bacteria are maintained under the medium during step b), c) and/or d) and/or during an additional step e), in order to identify or isolate bacteria which are viable or can be grown using the desired carbon source.

It should be understood that the above characteristics can be selected individually or in any combinations. For instance, the method can be used to identify bacteria which are viable or can be grown at a desired temperature and salinity, or at a desired temperature and pH, or at a desired temperature, pH and oxygenation condition.

Furthermore, the methods of this invention may comprise a further step of modifying, e.g., either biologically, genetically and/or chemically, the identified or isolated bacteria, or their DNA, by any process known per se in the art, said modification aiming e.g., to improve the viability, growth or functions of the said bacterium, e.g., enzymatic activity. Such modification step includes, without limitation, cell fusion, accelerated evolution, DNA shuffling, mutagenesis, insertion of eukaryote, prokaryote or synthetic nucleic acid (e.g., DNA) from another strain, or any genetic engineering technology. The modification may also include a step of introducing a marker gene (e.g., kanamycin resistance) in the bacterium. Said modification step can be carried out on the isolated bacteria, or at any earlier stage of the above process, e.g., on the sample of step a), for instance.

A further object of this invention is a bacterium obtainable by the above method.

More specifically, an object of this invention resides in an isolated bacterium, wherein said bacterium has the ability to grow in the presence of lignin or cellulose or xylan as the sole carbon source, at a temperature of at least 30° C., and to resist an UV treatment of 4 mJ/cm2. The combination of these features is unprecedented, and provides novel avenues in the exploitation of lignocellulosic biomass. In particular, the ability to resist the above UV treatment and to grow at 30° C. or more allows the use of the bacteria under special stringent industrial conditions compatible with the nature of biomass. The ability to grow in the presence of lignin, cellulose or xylan as the sole carbon source (i.e., to use lignin, cellulose or xylan as carbon source) makes the bacteria suitable to transform any type of lignocellulosic biomass.

In a further preferred embodiment, the bacterium has the ability to use lignin, cellulose and xylan as carbon source. Indeed, the inventors have identified bacteria which are able to degrade all major constituents of lignocellulosic biomass.

Furthermore, as illustrated in the experimental section, bacteria have been identified by the inventors which are able to grow either in aerobic or anaerobic condition, or both. In a particular and advantageous embodiment, the invention relates to bacteria as defined above which can be grown, or cultivated in both aerobic and anaerobic conditions. The invention indeed unexpectedly shows that bacteria can be operated under conditions, such as anaerobic conditions, suitable to produce high amounts of bioenergy products or metabolites from various substrates. The invention thus provides novel means and compositions for producing bioenergy products or metabolites from lignocellulosic biomass and/or lignocellulosic biomass components, namely cellulose, hemicellulose, and lignin, in a very efficient manner.

Preferred bacteria of this invention can hydrolyse lignocellulosic biomass to produce fermentable sugars, and can be cultivated in aerobic or anaerobic conditions.

Bacteria of this invention preferably belong to a genus selected from *Deinococcus, Bacillus, Microbacterium, Cellulosimicrobium, Methylobacterium, Sphingobacterium, Pseudomonas, Caldimonas, Paenibacillus, Gordonia, Rhodococcus, Stenotrophomonas, Novosphingobium, Sphingomonas, Flavobacterium, Sphingobium, Sphingopyxis,* or *Porphyrobacter.*

Preferred bacteria of this invention exhibit the following characteristics:
   viable or functional at high temperatures (e.g., around 30-70° C.),
   viable or functional in anaerobic conditions,
   resist a UV treatment of 4 mJ/cm2; and
   able to promote cellulose digestion to yield glucose.

Other preferred bacteria of this invention exhibit the following characteristics:
   viable or functional at high temperatures (e.g., around 30-70° C.),
   viable or functional in anaerobic conditions,
   resist a UV treatment of 4 mJ/cm2; and
   able to use lignin as carbon source.

Other preferred bacteria of this invention exhibit the following characteristics:
   viable or functional at high temperatures (e.g., around 30-70° C.),
   viable or functional in anaerobic conditions,
   resist a UV treatment of 4 mJ/cm2; and
   able to use xylan as carbon source.

Other preferred bacteria of this invention exhibit the following characteristics:
   viable or functional at high temperatures (e.g., around 30-70° C.),
   viable or functional in anaerobic conditions,
   resist a UV treatment of 4 mJ/cm2;
   able to use lignin as carbon source; and
   able to promote cellulose digestion to yield glucose; and/or
   able to promote xylan digestion to yield xylose; and/or
   able to use xylan as carbon source.

The bacterium may be maintained or cultivated in suitable culture medium such, as without limitation, PGY (Bacto-peptone 10 g/L, Yeast extract 5 g/L, glucose 1 g/L) or LB (Bacto-tryptone 10 g/L, Yeast extract 2.5 g/L, Sodium chloride 10 g/L). It should be understood that other suitable culture media are known to the skilled person (Buchanan et al, 1974, Difco, 1995) or may be prepared by the skilled person from such known media.

Specific illustrative examples of bacteria of this invention are provided in the experimental section, together with their isolation technique and properties. It should be understood that other bacteria may be isolated or characterized following the teaching of the present invention.

A further object of this invention resides in the use of bacteria as provided by the inventors, or extracts thereof, to produce valuable products from lignocellulosic biomass.

In this regard, the invention relates to the use of such a bacterium, or an extract thereof, to hydrolyse lignocellulosic biomass.

The invention also relates to the use of such a bacterium, or an extract thereof, to transform lignocellulosic biomass into bioenergy products or metabolites.

The invention also relates to a method of degrading lignocellulosic biomass into fermentable sugars, the method comprising exposing said lignocellulosic biomass to a bacterium of this invention, or an extract thereof.

The method is particularly suited to produce fermentable sugars selected from glucose, cellobiose, mannose, xylose, arabinose or galactose.

A further object of this invention is a reactor or fermentor comprising lignocellulosic biomass and a bacterium of the invention or an extract thereof.

A further object of this invention is a method of producing bioenergy products or metabolites, particularly ethanol, the method comprising exposing a lignocellulosic biomass to a bacterium of the invention, or an extract thereof. The method preferably further comprises a step of collecting said bioenergy products or metabolites.

A further object of this invention is a bioenergy product or metabolite obtained by the above methods.

Culture or exposition can be made in any suitable condition or environment allowing modification of the lignocellulosic biomass to produce bioenergy products or metabolites. In this regard, the method can be performed in a reactor, in a fermentor, outdoor, in the presence of suitable nutrients or additives, if needed. The method is typically conducted under pH conditions, temperature above 40° C., and in the presence of suitable substrates.

In the above methods, the step of culturing and/or growing the bacterium and the step of transforming the biomass into bioenergy products or metabolites can be carried out either simultaneously, or sequentially; and the step of collecting bioenergy products or metabolites can be carried out simultaneously with the first and/or the second step, or sequentially. In this regard, the biomass can be contacted with the bacterium under suitable conditions to allow expansion of said bacterium, thereby increasing the efficiency of the process. Alternatively, bacterial strains can be expanded separately, under suitable culture conditions, and subsequently added to the biomass. It should be understood that the precise amounts of bacteria used initially in order to efficiently transform biomass into substantial bioenergy products or metabolites can be adjusted by the skilled artisan depending on the type of bacteria, the type of biomass, and the culture conditions.

In a particular embodiment of the method, the bacteria are grown separately from biomass conversion.

In a particular embodiment, the method of the invention is performed in a reactor of conversion of biomass. By "reactor" is meant a conventional fermentation tank or any apparatus or system for biomass conversion specially designed to implement the invention and therefore consisting in particular of bioreactors, biofilters, rotary biological contactors, and other gaseous and/or liquid phase bioreactors for the treatment of biomass. The apparatus which can be used according to the invention can be used continuously or in batch loads.

In the reactor, to implement the method of the invention, at least one bacterium or bacterial extract of the invention is used, whilst said reactor is arranged and supplied so that physicochemical conditions are set up and maintained therein so that said bacterium is operational for the application under consideration and so that, optionally, bacterial growth is possible and preferably promoted therein.

In another embodiment of the method of the invention, the bacteria are grown in a reactor, during the conversion of biomass, whilst suitable physicochemical conditions are set up and maintained for this bacterial growth to be possible, and preferably promoted.

In alternative embodiments of the invention, the conversion of biomass is conducted under aerobiosis, anaerobiosis or under microaerobiosis.

Further aspects and advantages of the invention will be disclosed in the examples, which are illustrative and do not limit the scope of protection.

EXAMPLES

Materials and Methods

Selection Tests and Culture Media Composition

| 167 Thermus medium | | |
|---|---|---|
| Tryptone | 1 | g |
| Yeast extract | 1 | g |
| Agar | 28 | g |
| Nitrilotriacetic acid | 100 | mg |
| $CaSO_4 \times 2 H_2O$ | 40 | mg |
| $MgCl_2 \times 6 H_2O$ | 200 | mg |
| 0.01M Fe citrate | 0.5 | ml |
| Solution of trace elements (see below) | 0.5 | ml |
| Phosphate buffer (see below) | 100 | ml |
| $H_2O$ | 900 | ml |
| Adjust to pH 7.2 with NaOH, autoclave at 121° C. for 15 min. autoclave the phosphate buffer separately and add to the medium | | |

| Phosphate buffer | | |
|---|---|---|
| $KH_2PO_4$ | 5.44 | g |
| $Na_2HPO_4 \times 12 H_2O$ | 43 | g |
| $H_2O$ | 1000 | ml |
| Adjust to pH 7.2 | | |

Composition of Minimum Medium
  MOPS buffer 1× (ph7) containing: acid MOPS buffer 40 mM, $NH_4Cl$ 20 mM, KOH 10 mM, NaOH 10 mM, $CaCl_2$ 0.5 µM, $Na_2SO_4$ 0.276 mM, $MgCl_2$ 0.528 mM.
  A solution of micronutriments (pH5): $(NH_4)_6(MO_7)_{24}$ 3 nM, $H_3BO_3$ 400 nM, $CoCl_2$ 30 nM, $CuSO_4$ 10, nM, $MnCl_2$ 250 nM, $ZnSO_4$ 10 nM.
  Solution of vitamins, pH4.0, (1 µg/1 each): D-biotin, niacin, pyridoxal-HCl, thiamin-HCl, vitamin B12
  Source of phosphate: $K_2HPO_4$ 5.7 mM
  $FeCl_3$ 20 µM (prepared in a solution of sodium citrate then filtered).
Detection of the Cellulase Activity of the Bacterium:
Principle:
  The test is based on follow-up of the conversion of NAD into NADH during degradation of the cellulose. An increase in absorbency is then monitored at 340 nm following the supplier's instructions,
Detection of Ethanol Production:
  Ethanol can be quantified using two methods.
Enzymatic Method:

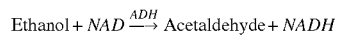

$$\text{Ethanol} + NAD \xrightarrow{ADH} \text{Acetaldehyde} + NADH$$

This method is based on follow-up of the conversion of NAD into NADH in the presence of ethanol and alcohol dehydrogenase.
  This reaction translates as in increase in absorbency at 340 nm. For this measurement, the Sigma N7160, kit can be used following the manufacturer's instructions.
Measurement by Reverse Phase High Performance Liquid Chromatography
  Conditions:
HPLC Gilson with automatic injector, detection by refractometry,
Column: Phenomenex Rezex ROA, 300 mm×7.8 mm Column temperature: 65° C.
Mobile phase: 0.005 N sulphuric acid
Flow rate: 0.600 ml/min First a calibration curve is made by injecting culture medium containing known concentrations of ethanol into the column. The peak area eluted at 22.26 min corresponding to ethanol is measured. A calibration curve is plotted.

Next, the quantity of ethanol produced by the bacterium is measured by injecting the culture supernatant into the column. The peak area eluted at 22.26 min and corresponding to ethanol is measured. The concentration of ethanol present in the supernatant is deduced by comparison with the calibration curve.

The detection and quantification of the other metabolites possibly produced in diverse proportions can be made following conventional methods of analysis and evaluation.

Example 1

Selection of Thermophilic UV-Resistant Bacteria which Use Cellulose as Carbon Source and Grow in Anaerobiosis (FIG. 1)

Thermophilic bacteria selected for their resistance to UV rays and isolated from environmental samples (3 treatments of 4 mJ/cm2 with an interval of 4 hours) are inoculated on a solid minimal culture medium sterilized by autoclaving (15 minutes at 120° C.) containing the carbon source of interest at 1%: carboxymethylcellulose (CMC; Fluka, France) or xylan from birchwood (Fluka, France). The minimal culture medium is made up of a MOPS buffer solution at pH7 and filtered: acid MOPS buffer 40 mM (Sigma, France), $NH_4Cl$ 20 mM, KOH 10 mM, NaOH 10 mM, $CaCl_2$ 0.5 μM, $Na_2SO_4$ 0.276 mM, $MgCl_2$ 0.528 mM), a solution of micronutriments at pH5 (($NH_4)_6(MO_7)_{24}$ 3 nM, $H_3BO_3$ 400 nM, $CoCl_2$ 30 nM, $CuSO_4$ 10 nM, $MnCl_2$ 250 nM, $ZnSO_4$ 10 nM), a solution of vitamins at pH4 (1 μg/L of D-biotin, niacin, pyridoxal-HCl, thiamin-HCl and vitamin B12), a solution of $K_2HPO_4$ at 5.7 mM as well as a solution of $FeCl_3$ at 20 μM in $NaH_2(C_3H_5O(COO)_3)$.

Conditions of anaerobiosis are ensured by the addition of a GENbag anaer (BioMérieux, France). After incubation in anaerobiosis at 45° C. for 4 to 5 days, the colonies using the carbon source present in the culture medium are visible (see FIG. 1).

The UV resistant bacterium designated M11-2F is able to grow in anaerobiosis and at 45° C. by using CMC as sole carbon source.

This bacterium is thus able to transform lignocellulosic biomass into valuable products under industrial conditions.

Example 2

Figure 2:
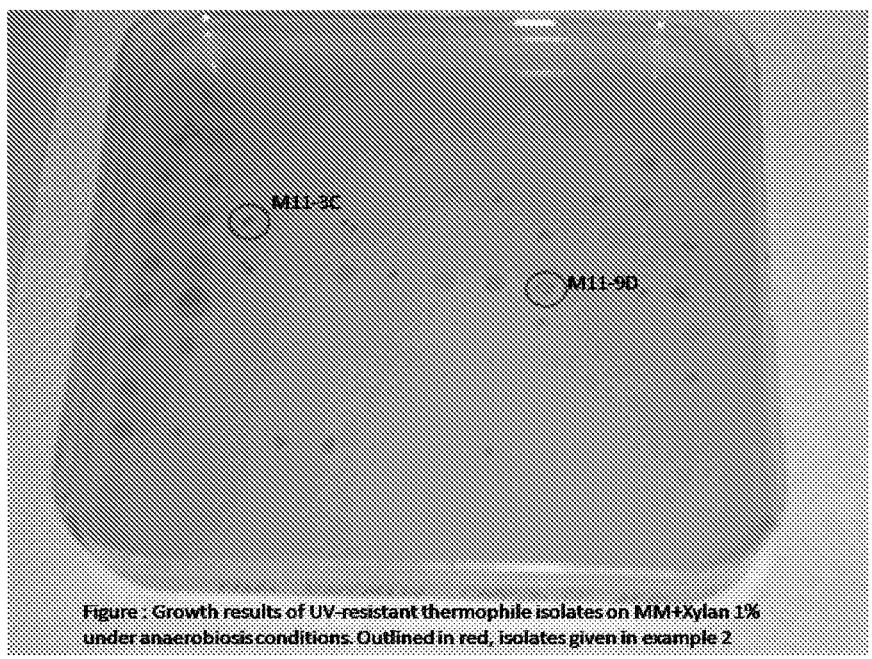
FIG. 2: growth results of UV-resistant thermophilic bacteria on MM+xylan1% under anaerobiosis conditions.

Selection of Thermophilic UV-Resistant Bacteria which Use Xylan in Anaerobiosis (FIG. 2)

Thermophilic bacteria selected for their resistance to UV rays from environmental samples (3 treatments of 4 mJ/cm2 with an interval of 4 hours) are inoculated on a solid minimal culture medium sterilized by autoclaving (15 minutes at 120° C.) containing the carbon source of interest at 1%: carboxymethylcellulose (CMC; Fluka, France) or xylan from birchwood (Fluka, France). The minimal culture medium is made up of a MOPS buffer solution at pH7 and filtered: acid MOPS buffer 40 mM (Sigma, France), $NH_4Cl$ 20 mM, KOH 10 mM, NaOH 10 mM, $CaCl_2$ 0.5 μM, $Na_2SO_4$ 0.276 mM, $MgCl_2$ 0.528 mM), a solution of micronutriments at pH5 (($NH_4)_6(MO_7)_{24}$ 3 nM, $H_3BO_3$ 400 nM, $CoCl_2$ 30 nM, $CuSO_4$ 10 nM, $MnCl_2$ 250 nM, $ZnSO_4$ 10 nM), a solution of vitamins at pH4 (1 μg/L of D-biotin, niacin, pyridoxal-HCl, thiamin-HCl and vitamin B12), a solution of $K_2HPO_4$ at 5.7 mM as well as a solution of $FeCl_3$ at 20 μM in $NaH_2(C_3H_5O(COO)_3)$.

Conditions of anaerobiosis are ensured by the addition of a GENbag anaer (BioMérieux, France). After incubation in anaerobiosis at 45° C. for 4 to 5 days, the colonies using the carbon source present in the culture medium are visible (see FIG. 2).

The UV resistant bacterium designated M11-3C is able to grow in anaerobiosis and at 45° C. by using xylan from birch wood as sole carbon source.

The UV resistant bacterium designated M11-9D is able to grow in anaerobiosis and at 45° C. on a culture medium containing either CMC or xylan as source of carbon.

These bacteria are thus able to transform lignocellulosic biomass into valuable products under industrial conditions.

Example 3

Figure 3:
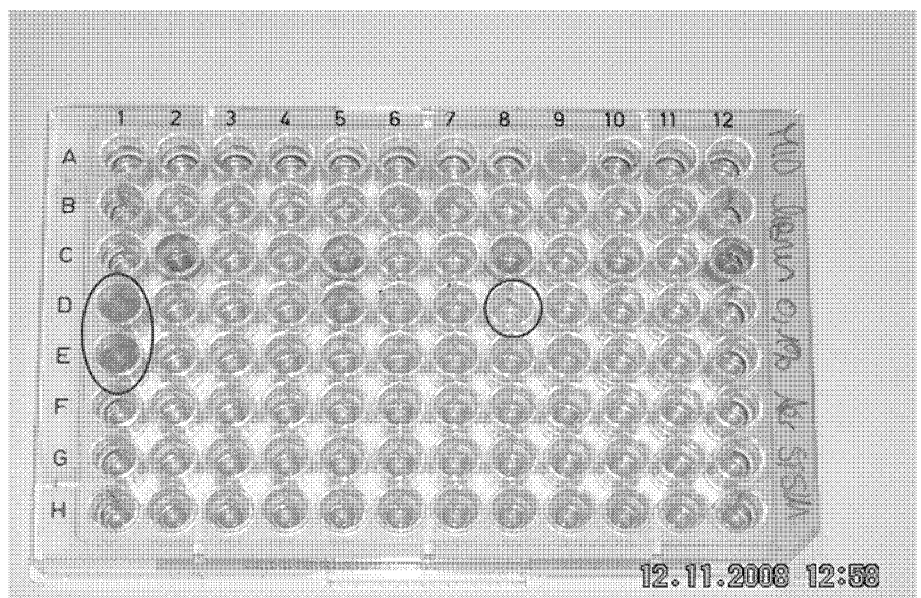
FIG. 3: growth results of UV-resistant pink isolates on MM+lignin 0.1% under aerobiosis conditions at 30° C. after 5 days. Outlined are isolates M10-1D and M10-1E, which are able to use lignin as sole carbon source, and M10-8D, which is able to degrade lignin.

Selection of UV-Resistant Bacteria which are Able to Use Lignin as Carbon Source (FIG. 3)

Bacteria selected for their resistance to UV rays from environmental samples (3 treatments of 4 mJ/cm2 with an interval of 4 hours) are inoculated on a solid minimal culture medium containing lignin at 0.1% (Sigma, France). Composition of the minimum culture medium is described in the previous examples. After incubation at 30° C. for 4 to 5 days, the colonies using the lignin present in the culture medium as carbon source are visible (bacteria which degrade the lignin decolorize the medium). The results are depicted in FIG. 3 and in the following Tables 1 and 2.

TABLE 1

| Biotope Environment | Name Strain | Isolation t° C. | Isolation medium | cultured closest neighbors | aerobiosis Lignin | anaerobiosis CMC + Xylan |
|---|---|---|---|---|---|---|
| Muck | M5-6H | 30° C. | PGY | *Bacillus* | + | + |
| animal dejection | M6-2H | 30° C. | PGY | *Microbacterium* | + | + |
| stones | M6-4H | 30° C. | PGY | *Cellulosimicrobium* | + | + |
|  | M8-1B | 30° C. | PGY | *Methylobacterium* | + | + |
|  | M8-1H | 30° C. | PGY | *Methylobacterium* | + | + |
|  | M8-2B | 30° C. | PGY | *Methylobacterium* | + | + |
|  | M8-3A | 30° C. | PGY | *Methylobacterium* | + | + |
|  | M8-3C | 30° C. | PGY | *Methylobacterium* | + | + |
|  | M8-4A | 30° C. | PGY | *Methylobacterium* | + | + |
|  | M8-4B | 30° C. | PGY | *Methylobacterium* | + | + |
|  | M8-4H | 30° C. | PGY | *Methylobacterium* | + | + |
|  | M8-5A | 30° C. | PGY | *Methylobacterium* | + | + |

TABLE 1-continued

| Biotope Environment | Name Strain | Isolation t° C. | Isolation medium | cultured closest neighbors | aerobiosis Lignin | anaerobiosis CMC + Xylan |
|---|---|---|---|---|---|---|
| | M8-5B | 30° C. | PGY | *Methylobacterium* | + | + |
| | M8-6G | 30° C. | PGY | *Methylobacterium* | + | + |
| | M8-7E | 30° C. | PGY | *Methylobacterium* | + | + |
| moss | M8-9E | 30° C. | PGY | *Methylobacterium* | + | + |
| | M8-9H | 30° C. | PGY | *Methylobacterium* | + | + |
| | M8-11C | 30° C. | PGY | *Methylobacterium* | + | + |
| animal dejection | M9-2E | 30° C. | PGY | *Sphingobacterium* | + | + |
| | M9-3E | 30° C. | PGY | *Sphingobacterium* | + | + |
| | M9-3F | 30° C. | PGY | *Sphingobacterium* | + | + |
| cow dejection | M9-7D | 30° C. | PGY | *Pseudomonas* | + | + |
| | M9-7E | 30° C. | PGY | Uncultured bacterium isolated from Argalis sheep feces | + | + |

TABLE 2

| | | | | cultured | Carbon source | | | | | |
|---|---|---|---|---|---|---|---|---|---|---|
| | | | | | Aerobiosis | | | Anaerobiosis | | |
| Biotope | Name | t° isolation | Isolation medium | closest neighbors | CMC | Xylane | Lignin | CMC | Xylane | Lignin |
| Water | MX1-1B | 45° C. | MM + Xyl 1% | *Bacillus* | + | + | + | + | + | + |
| Water | MX1-6G | 45° C. | MM + Xyl 1% | *Caldimonas* | + | + | + | | + | − |
| Water | MX1-7B | 45° C. | MM + Xyl 1% | *Paenibacillus* | + | + | + | + | + | + |
| Water | MX1-7C | 45° C. | MM + Xyl 1% | *Paenibacillus* | + | + | + | + | + | + |
| Water | MC1-1D | 45° C. | MM + CMC 1% | *Gordonia* | + | + | + | + | + | − |
| Water | MC1-1G | 45° C. | MM + CMC 1% | *Paenibacillus* | + | + | + | − | − | − |
| Water | MC1-2A | 45° C. | MM + CMC 1% | *Bacillus* | + | + | + | − | + | − |
| Sediment | MC1-2D | 45° C. | MM + CMC 1% | *Paenibacillus* | + | + | + | − | + | − |
| Water | M10-1D | 30° C. | PGY | *Rhodococcus* | + | + | + | nd | nd | nd |
| | M10-1E | 30° C. | PGY | *Rhodococcus* | + | + | + | nd | nd | nd |
| | M10-8D | 30° C. | PGY | *Stenotrophomonas* | + | + | + | nd | nd | nd |

All these bacteria are thus able to transform lignocellulosic biomass into valuable products under industrial conditions. Using of lignin as carbon source by bacteria belonging to *Sphingobacterium*, *Microbacterium* or *Cellulosimicrobium* genera has never been described until now.

Example 4

Lignocellulosic Biomass Conversion

A bacteria sample from a liquid culture performed in rich medium, is washed with deionized water before inoculating (1/10) 20 ml-minimal medium containing acid MOPS buffer 40 mM (Sigma, France), $NH_4Cl$ 20 mM, KOH 10 mM, NaOH 10 mM, $CaCl_2$ 0.5 µM, $Na_2SO_4$ 0.276 mM, $MgCl_2$ 0.528 mM), a solution of micronutriments at pH5 $((NH_4)_6(MO_7)_{24}$ 3 nM, $H_3BO_3$ 400 nM, $CoCl_2$ 30 nM, $CuSO_4$ 10 nM, $MnCl_2$ 250 nM, $ZnSO_4$ 10 nM), a solution of vitamins at pH4 (1 µg/L of D-biotin, niacin, pyridoxal-HCl, thiamin-HCl and vitamin B12), a solution of $K_2HPO_4$ at 5.7 mM as well as a solution of $FeCl_3$ at 20 µM in $NaH_2(C_3H_5O(COO)_3)$. Paper journal and/or Whatman paper is used as source of lignocellulosic biomass and carbon source. About 140 mg of paper journal is added to the culture medium described above. The degradation of the paper journal and/or Whatman paper is monitored during several weeks and compare to the control tube (without any bacteria in the culture medium).

Figure 4:
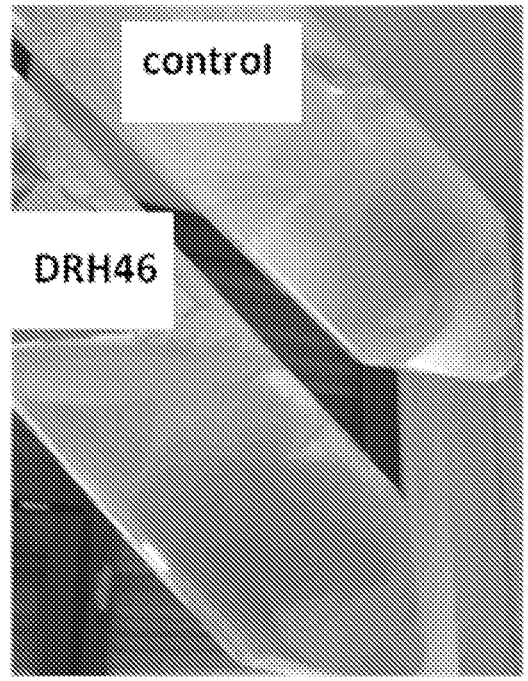
FIG. 4: *Deinococcus* strain DRH46 is able to degrade paper journal.

The results are depicted in FIG. 4. The *Deinococcus* strain DRH46 is able to degrade paper journal and/or Whatman paper. The degradation is visualized with the release of paper fibers in the culture medium which become cloudy after several weeks of growth (compare to the control tube).

Example 5

Selection of UV-Resistant Cellulolytic and Xylanolytic *Deinococci* Producing Detectable Level of Ethanol Bacteria selected for their resistance to UV rays from environmental samples (3 treatments of 4 mJ/cm2 with an interval of 4 hours)) are inoculated at 45° C. on a minimal liquid medium containing Whatman I filter paper or xylan, as sole carbon source of lignocellulosic substrate. Composition of the minimum culture medium is described in the previous examples. The paper whatman I is degraded after several weeks of incubation with bacteria at 45° C., whereas no degradation was seen of whatman I filter paper treated in the same way as described above but containing no bacteria (control). In addition, an increase in opacity of culture medium containing bacteria grown in xylan as sole carbon source was seen after several days of incubation at 45° C. compared to the control medium containing no bacteria indicating a bacterial growth in such conditions. The metabolic properties of the strains are then determined to assess their ability to produce ethanol. Among various strains identified, the following may be mentioned, which is cellulolytic, xylanolytic, and produces ethanol.

| Species | Strain name | Starch | Sucrose | Xylan | Whatman I | Glucose | EtOH production (%) |
|---|---|---|---|---|---|---|---|
| D. murrayi | M13-8D | + | + | + | + | + | 0.016 |

This example further illustrates the efficacy of the method of the present invention, and the ability to isolate bacteria having the selected remarkable properties when applying the claimed method to various samples.

The invention claimed is:

1. A method of producing bioenergy products or metabolites, the method comprising exposing a lignocellulosic biomass to a bacterium to produce fermentable sugars, and fermenting said sugars into bioenergy products or metabolites, wherein said bacterium is selected from:
   a) a bacterium which can grow in the presence of lignin as a sole carbon source, at a temperature of at least 30° C., and resist 3 UV treatments of 4 mJ/cm$^2$ carried out at an interval of 4 hours; or
   b) a bacterium which has the ability to utilize cellulose and xylan as carbon sources, at a temperature of at least 30° C., and to resist 3 UV treatments of 4 mJ/cm$^2$ carried out at an interval of 4 hours.

2. The method of claim 1, further comprising collecting said bioenergy products or metabolites.

3. The method of claim 1, wherein said bacterium can use lignin, cellulose and xylan as carbon sources.

4. The method of claim 1, wherein said bacterium can be cultivated in aerobic and anaerobic conditions.

5. The method of claim 1, wherein said bacterium belongs to a genus selected from *Deinococcus, Bacillus, Microbacterium, Cellulosimicrobium, Methylobacterium, Sphingobacterium, Pseudomonas, Caldimonas, Paenibacillus, Gordonia, Rhodococcus, Stenotrophomonas, Novosphingobium, Sphingomonas, Flavobacterium, Sphingobium, Sphingopyxis*, or *Porphyrobacter*.

6. The method of claim 1, wherein said bacterium is obtained by a method comprising:
   a) providing a sample comprising bacteria;
   b) subjecting the sample to a cell-destructing UV irradiation comprising at least 3 UV treatments of 4 mJ/cm$^2$ carried out at an interval of 4 hours; and
   c) culturing said UV treated sample in/on a selection medium containing: lignin as the sole carbon source, cellulose as the sole carbon source, xylan as the sole carbon source or a combination of cellulose and xylan as the sole carbon sources; and
   d) isolating from said cultured UV treated sample, a bacterium which utilizes lignin as the sole carbon source in the selection medium, utilizes cellulose as the sole carbon source in the selection medium, utilizes xylan as the sole carbon source in the selection medium or utilizes both cellulose and xylan as sole carbon sources in the selection medium.

7. The method of claim 1, wherein the lignocellulosic biomass comprises unprocessed material of biological origin.

8. The method of claim 7, wherein the unprocessed material of biological origin is selected from forestry products, agricultural products, or aquatic products.

9. The method of claim 1, wherein the fermentable sugar is selected from glucose, cellobiose, mannose, xylose, arabinose or galactose.

10. The method of claim 1, wherein the bioenergy product is a biofuel.

11. A method of producing a biofuel, the method comprising exposing a lignocellulosic biomass to a bacterium to produce fermentable sugars, and fermenting said sugars into biofuel, wherein said bacterium is selected from:
   a) a bacterium which can grow in the presence of lignin as a sole carbon source, at a temperature of at least 30° C., and resist 3 UV treatments of 4 mJ/cm$^2$ carried out at an interval of 4 hours;
   b) a bacterium which has the ability to utilize cellulose as a sole carbon source, at a temperature of at least 30° C., and to resist 3 UV treatments of 4 mJ/cm$^2$ carried out at an interval of 4 hours;
   c) a bacterium which has the ability to utilize xylan as a sole carbon source, at a temperature of at least 30° C., and to resist 3 UV treatments of 4 mJ/cm$^2$ carried out at an interval of 4 hours; or
   d) a bacterium which has the ability to utilize both cellulose and xylan as carbon sources, at a temperature of at least 30° C., and to resist 3 UV treatments of 4 mJ/cm$^2$ carried out at an interval of 4 hours.

* * * * *